US009206385B2

(12) United States Patent
Koeda et al.

(10) Patent No.: US 9,206,385 B2
(45) Date of Patent: *Dec. 8, 2015

(54) THERMAL CYCLER

(71) Applicant: Seiko Epson Corporation, Tokyo (JP)

(72) Inventors: Hiroshi Koeda, Suwa (JP); Toshiro Murayama, Fujimi (JP)

(73) Assignee: Seiko Epson Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,462

(22) Filed: Jun. 5, 2013

(65) Prior Publication Data

US 2013/0330818 A1    Dec. 12, 2013

(30) Foreign Application Priority Data

Jun. 6, 2012 (JP) ................................. 2012-129336

(51) Int. Cl.
  *C12M 1/34* (2006.01)
  *B01L 7/00* (2006.01)

(52) U.S. Cl.
  CPC ................ *C12M 41/12* (2013.01); *B01L 7/525* (2013.01); *B01L 7/5255* (2013.01); *B01L 7/54* (2013.01); *B01L 2300/1827* (2013.01); *B01L 2400/0445* (2013.01); *B01L 2400/0469* (2013.01)

(58) Field of Classification Search
  CPC ................ B01L 2300/1827; B01L 2400/0445; B01L 2400/0469; B01L 7/525; B01L 7/5255; B01L 7/54; C12M 41/12
  USPC ...................................................... 435/303.1
  See application file for complete search history.

(56) References Cited

U.S. PATENT DOCUMENTS

| 6,875,602 | B2 | 4/2005 | Gutierrez |
| 8,932,833 | B2 | 1/2015 | Yamaguchi et al. |
| 2002/0155475 | A1 | 10/2002 | Vischer |
| 2007/0099189 | A1 | 5/2007 | Gomez-Elvira Rodriguez et al. |
| 2008/0176290 | A1 | 7/2008 | Joseph et al. |

(Continued)

FOREIGN PATENT DOCUMENTS

| JP | 2009-136250 A | 6/2009 |
| WO | WO-2012-073484 A1 | 6/2012 |

OTHER PUBLICATIONS

Qiagen OneStep RT-PCR Kit, Quick-Start Protocol, published Jan. 2011, pp. 1-4.

*Primary Examiner* — Nathan Bowers
*Assistant Examiner* — Lydia Edwards
(74) *Attorney, Agent, or Firm* — Harness, Dickey & Pierce, P.L.C.

(57) ABSTRACT

A thermal cycler includes: a first mounting unit and a second mounting unit which are cylindrical; a temperature gradient forming unit which forms a temperature gradient along mounting directions of the first mounting unit and the second mounting unit; and a driving mechanism which rotates the first mounting unit, the second mounting unit, and the temperature gradient forming unit around a rotating shaft having a component perpendicular to a direction in which gravity is applied and a component intersecting the mounting directions of the first mounting unit and the second mounting unit, wherein the first mounting unit and the second mounting unit are disposed on opposite sides to each other with the rotating shaft interposed therebetween, the mounting direction of the first mounting unit and the mounting direction of the second mounting unit are in the same direction.

13 Claims, 6 Drawing Sheets

(56) References Cited

U.S. PATENT DOCUMENTS

| | | |
|---|---|---|
| 2011/0183378 A1* | 7/2011 | Takagi et al. ............ 435/91.2 |
| 2011/0189660 A1 | 8/2011 | Koeda |
| 2011/0256590 A1 | 10/2011 | Koeda |
| 2012/0122160 A1* | 5/2012 | Saito et al. ............ 435/91.2 |
| 2012/0145260 A1 | 6/2012 | Koeda |
| 2012/0225001 A1 | 9/2012 | Koeda |
| 2012/0301367 A1 | 11/2012 | Koeda |
| 2013/0210081 A1 | 8/2013 | Koeda |

* cited by examiner

| COMPOSITION | PRESERVATION CONCENTRATION | FINAL CONCENTRATION | LIQUID AMOUNT [uL] |
|---|---|---|---|
| SuperScript III Platinum | | | 0.2 |
| Buffer | 2x | 1x | 5 |
| F primer | 40uM | 0.8uM | 0.2 |
| R primer | 40uM | 0.8uM | 0.2 |
| Probe | 10uM | 0.2uM | 0.2 |
| Distilled Water | | | 3.2 |
| RNA | | | 1 |
| total | | | 10 |

FIG. 7

| InfA F primer | 5'- GAT CRA TCC TGT CAC CTC TGA C -3' |
|---|---|
| InfA R primer | 5'- AGG GCA TTY TGG ACA AAK CGT CTA -3' |
| InfA Probe | 5'- TGC AGT CCT CGC TCA CTG GGC ACG -3' |
| SW InfA F primer | 5'- GCA CGG TCA GCA CTT ATY CTR AG -3' |
| SW InfA R primer | 5'- GTG RGC TGG GTT TTC ATT TGG TC -3' |
| SW InfA Probe | 5'- CYA CTG CAA GCC CAT ACA CAC AAG CAG CA -3' |
| SW H1 F primer | 5'- GTG CTA TAA ACA CCA GCC TYC CA -3' |
| SW H1 R primer | 5'- CGG GAT ATT CCT TAA TCC TGT RGC -3' |
| SW H1 Probe | 5'- CA GAA TAT ACA TCC RGT CAC AAT TGG ARA A -3' |
| RNaseP F primer | 5'- AGA TTT GGA CCT GCG AGC G -3' |
| RNaseP R primer | 5'- GAG CGG CTG TCT CCA CAA GT -3' |
| RNaseP Probe | 5'- TTC TGA CCT GAA GGC TCT GCG CG -3' |

FIG. 8

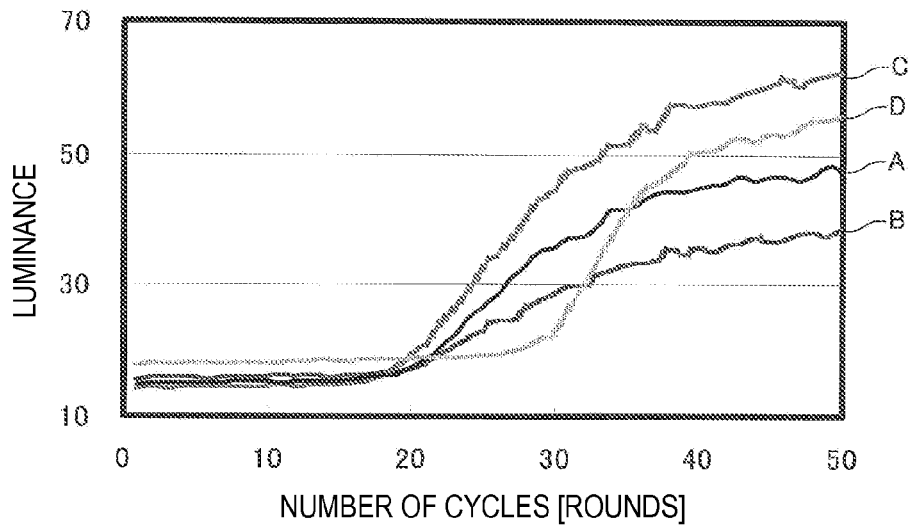

FIG. 9

THERMAL CYCLER

BACKGROUND

1. Technical Field

The present invention relates to a thermal cycler.

2. Related Art

In recent years, due to the development of a technique using genes, medical treatments using gene technology such as genetic diagnosis and gene therapy have received attention. Additionally, many methods using genes for species identification and breed improvements in the agriculture and stock-breeding field have been developed. As a technique for using genes, a technique such a PCR (Polymerase Chain Reaction) method or the like has been widely supplied. Presently, the PCR method is a technique essential to elucidation of information of biological materials.

The PCR method is a method of performing thermal cycling on a solution (reaction liquid) containing a nucleic acid as an amplification object (target nucleic acid) and a reagent to amplify a target nucleic acid. The thermal cycling is a treatment in which the reaction liquid is periodically subjected to two or more levels of temperatures. In the PCR method, a method of performing two stages or three stages of thermal cycling is common.

In the PCR method, generally, a container for a biochemical reaction, called a tube or a biological sample reaction chip (biochip) is used. However, in the method according to the related art, there are problems in that the amount of reagents needed and the like is large, an apparatus for realizing thermal cycling needed for the reaction is complex, and thus the reaction takes time. Therefore, a biochip or a reaction apparatus for performing PCR with good accuracy using a minute amount of reagent or analyte for a short time is needed.

In order to solve the problems, in JP-A-2009-136250, a biological sample reaction apparatus is disclosed in which a biological sample reaction chip filled with a reaction liquid and a liquid which is not blended with the reaction liquid and has a smaller specific gravity than the reaction liquid is rotated around a rotating shaft in a horizontal direction to move the reaction liquid and perform thermal cycling thereon.

In the biological sample reaction apparatus disclosed in JP-A-2009-136250, since the biological sample reaction chip is mounted on the apparatus having a temperature distribution that is symmetrical with respect to the rotating shaft to be rotated, in order to perform reactions having the same time conditions at the same timing using a plurality of reaction containers, mounting units for the reaction containers can be provided only in a direction along the rotating shaft (depth direction), and thus there is a limitation to a reduction in the size of the apparatus.

SUMMARY

An advantage of some aspects of the invention is to provide a thermal cycler appropriate for a size reduction.

Application Example 1

This application example is directed to a thermal cycler including: a first mounting unit and a second mounting unit; a temperature gradient forming unit which forms a temperature gradient along mounting directions of the first mounting unit and the second mounting unit; and a driving mechanism which rotates the first mounting unit, the second mounting unit, and the temperature gradient forming unit around a rotating shaft having a component perpendicular to a direction in which gravity is applied and a component intersecting the mounting directions of the first mounting unit and the second mounting unit, wherein the first mounting unit and the second mounting unit are disposed on opposite sides to each other with the rotating shaft interposed therebetween, the mounting direction of the first mounting unit and the mounting direction of the second mounting unit are in the same direction, and the temperature gradient forming unit forms the temperature gradient in the same direction in the first mounting unit and the second mounting unit.

According to this application example, since the rotating shaft has the component perpendicular to the direction in which gravity is applied and the component intersecting the mounting directions of the first and second mounting units, when the driving mechanism rotates the first and second mounting units, the position of the lowermost point or the uppermost point in the flow path of the reaction container in the direction in which gravity is applied is changed, in the case where the reaction containers are mounted on the first and second mounting units. Accordingly, the reaction liquid moves in the flow path of the reaction container having a temperature gradient formed by the temperature gradient forming unit. Therefore, thermal cycling can be performed on the reaction liquid that fills the reaction container. In addition, while the driving mechanism holds the first mounting unit, the second mounting unit, and the temperature gradient forming unit in a predetermined arrangement, the reaction liquid can be held at a predetermined temperature. Therefore, the thermal cycler capable of easily controlling a heating time of the reaction liquid can be realized. In addition, the first and second mounting units are disposed on the opposite sides with the rotating shaft interposed therebetween, the mounting direction of the first mounting unit and the mounting direction of the second mounting unit are in the same direction, and the temperature gradient forming unit forms a temperature gradient in the same direction in the first mounting unit and the second mounting unit. Therefore, reactions having the same time conditions can be performed at the same timing using the reaction container mounted on the first mounting unit and the reaction container mounted on the second mounting unit. The first and second mounting units do not need to be provided separately in the direction along the rotating shaft. Therefore, the thermal cycler that is appropriate for a size reduction can be realized.

Application Example 2

In the thermal cycler according to the application example described above, it is preferable that a control unit which controls the driving mechanism be further included, the control unit rotate an arrangement of the first mounting unit, the second mounting unit, and the temperature gradient forming unit between a first arrangement and a second arrangement different from the first arrangement, and in a case of a rotation from the first arrangement to the second arrangement and in a case of a rotation from the second arrangement to the first arrangement, the control unit control the driving mechanism to rotate the first mounting unit, the second mounting unit, and the temperature gradient forming unit in reverse directions.

According to this application example, in the case of a rotation from the first arrangement to the second arrangement and in the case of a rotation from the second arrangement to the first arrangement, the first mounting unit, the second mounting unit, and the temperature gradient forming unit are rotated in the opposite direction. Accordingly, a mechanism for reducing twisting of wiring of the apparatus caused by the rotations is unnecessary. Therefore, the thermal cycler that is appropriate for a size reduction can be realized.

Application Example 3

This application example is directed to a thermal cycler including: a first mounting unit and a second mounting unit; a first heating unit and a second heating unit provided to be separated from each other in a mounting direction of the first mounting unit; a third heating unit and a fourth heating unit provided to be separated from each other in a mounting direction of the second mounting unit; and a driving mechanism which rotates the first mounting unit, the second mounting unit, the first heating unit, the second heating unit, the third heating unit, and the fourth heating unit around a rotating shaft having a component perpendicular to a direction in which gravity is applied and a component intersecting the mounting directions of the first mounting unit and the second mounting unit, wherein the first mounting unit and the second mounting unit are disposed on opposite sides to each other with the rotating shaft interposed therebetween, the mounting direction of the first mounting unit and the mounting direction of the second mounting unit are in the same direction, the first heating unit and the third heating unit are set to a first temperature, the second heating unit and the fourth heating unit are set to a second temperature different from the first temperature, the first heating unit is provided on a side closer to the rotating shaft than the second heating unit, and the fourth heating unit is provided on a side closer to the rotating shaft than the third heating unit.

According to this application example, since the rotating shaft has the component perpendicular to the direction in which gravity is applied and the component intersecting the mounting directions of the first and second mounting units, when the driving mechanism rotates the first and second mounting units, the position of the lowermost point or the uppermost point in the flow path of the reaction container in the direction in which gravity is applied is changed, in the case where the reaction containers are mounted on the first and second mounting units. Accordingly, the reaction liquid moves in the flow path of the reaction container having a temperature gradient formed by the first, second, third, and fourth heating units. Therefore, thermal cycling can be performed on the reaction liquid that fills the reaction container. In addition, while the driving mechanism holds the first and second mounting units and the first, second, third, and fourth heating units in a predetermined arrangement, the reaction liquid can be held at a predetermined temperature. Therefore, the thermal cycler capable of easily controlling a heating time of the reaction liquid can be realized. In addition, the first and second mounting units are disposed on the opposite sides with the rotating shaft interposed therebetween, the mounting direction of the first mounting unit and the mounting direction of the second mounting unit are in the same direction, the first heating unit and the third heating unit are set to the first temperature, the second heating unit and the fourth heating unit are set to the second temperature different from the first temperature, the first heating unit is provided on the side closer to the rotating shaft than the second heating unit, and the fourth heating unit is provided on a side closer to the rotating shaft than the third heating unit. Accordingly, a temperature gradient is formed in the same direction in the reaction container mounted on the first mounting unit and in the reaction container mounted on the second mounting unit. Therefore, reactions having the same time conditions can be performed at the same timing using the reaction container mounted on the first mounting unit and the reaction container mounted on the second mounting unit. The first and second mounting units do not need to be provided separately in the direction along the rotating shaft. Therefore, the thermal cycler that is appropriate for a size reduction can be realized.

Application Example 4

In the thermal cycler according to the application example described above, it is preferable that a control unit which controls the driving mechanism be further included, the control unit rotate an arrangement of the first mounting unit, the second mounting unit, the first heating unit, the second heating unit, the third heating unit, and the fourth heating unit between a first arrangement and a second arrangement different from the first arrangement, and in a case of a rotation from the first arrangement to the second arrangement and in a case of a rotation from the second arrangement to the first arrangement, the control unit control the driving mechanism to rotate the first mounting unit, the second mounting unit, the first heating unit, the second heating unit, the third heating unit, and the fourth heating unit in reverse directions.

According to this application example, in the case of a rotation from the first arrangement to the second arrangement and in the case of a rotation from the second arrangement to the first arrangement, the first and second mounting units and the first, second, third, and fourth heating units are rotated in the opposite direction. Accordingly, a mechanism for reducing twisting of wiring of the apparatus caused by the rotations is unnecessary. Therefore, the thermal cycler that is appropriate for a size reduction can be realized.

BRIEF DESCRIPTION OF THE DRAWINGS

The invention will be described with reference to the accompanying drawings, wherein like numbers reference like elements.

FIG. 7 is a table showing the composition of a reaction liquid in Example.

FIG. 8 is a table showing the base sequences of forward primers (F primer), reverse primers (R primer), and probes (Probe) corresponding to influenza type A (InfA), swine influenza type A (SW InfA), swine influenza type H1 (SW H1), and ribonuclease P (RNase P).

FIG. 9 is a graph showing the relationship between the number of cycles of a thermal cycling treatment and the measured luminance in the Example.

DESCRIPTION OF EXEMPLARY EMBODIMENTS

Hereinafter, exemplary embodiments of the invention will be described in detail with reference to the drawings. In addition, the embodiments described hereinafter do not unfairly limit the contents of the invention described in the aspects. In addition, it cannot be said that all the configurations described hereinafter are the essential configuration requirements of the invention. The drawings are provided for convenience of description.

1. Entire Configuration of Thermal Cycler According to this Embodiment

Figure 1:
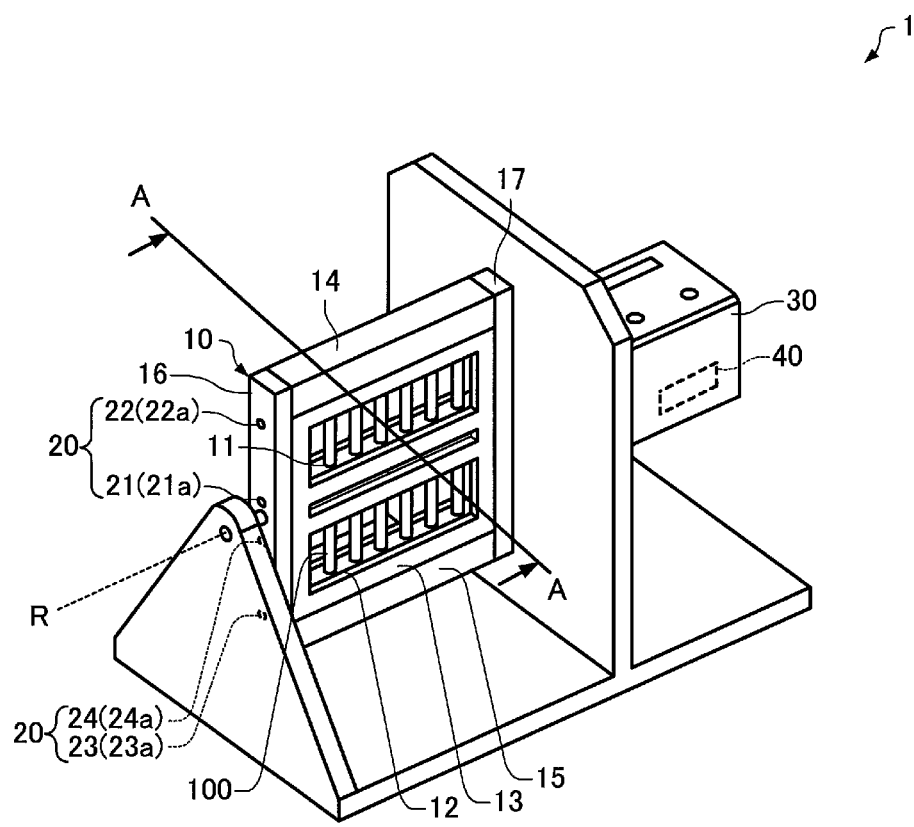
FIG. 1 is a perspective view of a thermal cycler according to an embodiment.
Figure 2:
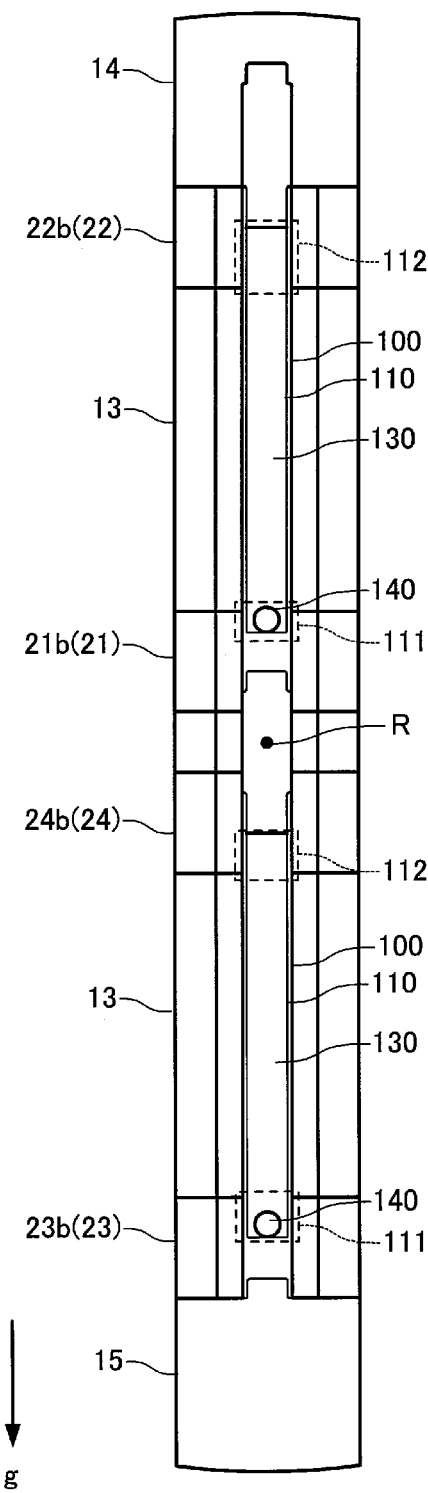
FIG. 2 is a vertical cross-sectional view taken along the line A-A of FIG. 1.

FIG. 1 is a perspective view of a thermal cycler 1 according to this embodiment. FIG. 2 is a vertical cross-sectional view taken along the line A-A of FIG. 1. In FIG. 2, the arrow g indicates a direction in which gravity is applied.

The thermal cycler 1 according to this embodiment includes: a first mounting unit 11; a second mounting unit 12; a temperature gradient forming unit 20 which forms a temperature gradient in mounting directions of the first mounting unit 11 and the second mounting unit 12; and a driving mechanism 30 which rotates the first mounting unit 11, the second mounting unit 12, and the temperature gradient forming unit 20 around a rotating shaft R having a component perpendicular to the direction in which gravity is applied and a component intersecting the mounting directions of the first mounting unit 11 and the second mounting unit 12.

In the example illustrated in FIG. 1, the thermal cycler 1 is configured to include a main body 10 and the driving mechanism 30. As illustrated in FIG. 1, the main body 10 is configured to include the first mounting unit 11, the second mounting unit 12, and the temperature gradient forming unit 20. In the example illustrated in FIGS. 1 and 2, the temperature gradient forming unit 20 is configured to include a first heating unit 21, a second heating unit 22, a third heating unit 23, and a fourth heating unit 24.

The first and second mounting units 11 and 12 have a structure to which a reaction container 100 is mounted. In the example illustrated in FIGS. 1 and 2, the first and second mounting units 11 and 12 of the thermal cycler 1 have a cylindrical slot structure in which the reaction container 100 is inserted into a through-hole provided in a frame 13 of the main body 10 to be mounted thereon. In the example illustrated in FIGS. 1 and 2, the mounting directions of the first and second mounting units 11 and 12 are directions in which the through-hole extends. In the example illustrated in FIG. 2, the first mounting unit 11 has a structure in which the reaction container 100 is inserted into holes that penetrate a first heat block 21b of the first heating unit 21 and a second heat block 22b of the second heating unit 22. In addition, in the example illustrated in FIG. 2, the second mounting unit 12 has a structure in which the reaction container 100 is inserted into holes that penetrate a third heat block 23b of the third heating unit 23 and a fourth heat block 24b of the fourth heating unit 24. The first, second, third, and fourth heat blocks 21b, 22b, 23b, and 24b will be described later. The number of first and second mounting units 11 and 12 provided in the main body 10 may be in the plural, and in the example illustrated in FIG. 1, six first mounting units 11 and six second mounting units 12 are provided in the main body 10. In addition, in the example illustrated in FIGS. 1 and 2, the first mounting units 11 are configured as parts of the first and second heating units 21 and 22, and the second mounting units 12 are configured as parts of the third and fourth heating units 23 and 24. However, as long as the positional relationship between the two is not changed when the driving mechanism 30 is operated, the first mounting unit 11 and the first and second heating units 21 and 22 may be configured as different members, and the second mounting unit 12 and the third and fourth heating units 23 and 24 may be configured as different members.

In this embodiment, the example in which the first and second mounting units 11 and 12 have the cylindrical slot structure is described. However, the first and second mounting units 11 and 12 may have a structure that can hold the reaction container 100. For example, a structure in which the reaction container 100 is inserted into a cylindrical recess that fits the shape of the reaction container 100 may be employed.

In the thermal cycler 1 of this embodiment, the first mounting unit 11 and the second mounting unit 12 are disposed on opposite sides with the rotating shaft R interposed therebetween. In addition, the mounting direction of the first mounting unit 11 and the mounting direction of the second mounting unit 12 are in the same direction. In the example illustrated in FIGS. 1 and 2, the mounting direction of the first mounting unit 11 and the mounting direction of the second mounting unit 12 are on the same straight line. Therefore, in the thermal cycler 1 of this embodiment, a direction in which a reaction liquid 140 moves in the reaction container 100 mounted on the first mounting unit 11 and a direction in which a reaction liquid 140 moves in the reaction container 100 mounted on the second mounting unit 12 are in the same direction.

The temperature gradient forming unit 20 forms a temperature gradient along the mounting directions of the first and second mounting units 11 and 12. That is, when the reaction containers 100 are mounted on the first and second mounting units 11 and 12, the temperature gradient forming unit 20 forms a temperature gradient in a direction in which the reaction liquid 140 moves with respect to a flow path 110. Here, "to form a temperature gradient" means to form a state in which temperature changes along a predetermined direction. Therefore, "a temperature gradient is formed in the direction in which the reaction liquid 140 moves" means that a state in which temperature changes along the direction in which the reaction liquid 140 moves is formed. In "the state in which temperature changes along a predetermined direction" for example, temperature may monotonically increase or decrease along the predetermined direction, temperature may be changed to increase and then changed to decrease along the predetermined direction, or temperature may be changed to decrease and then changed to increase partway.

In addition, the temperature gradient forming unit 20 forms a temperature gradient in the same direction in the first and second mounting units 11 and 12. That is, the temperature gradient forming unit 20 forms a temperature gradient in the same direction in the flow path 110 of the reaction container 100 mounted on the first mounting unit 11 and in the flow path 110 of the reaction container 100 mounted on the second mounting unit 12.

In the main body 10 of the thermal cycler 1, illustrated in FIGS. 1 and 2, the first heating unit 21 of the temperature gradient forming unit 20 is disposed on a side relatively far from a top plate 14 in the first mounting unit 11 (a side relatively close to a bottom plate 15 and a side relatively close to the rotating shaft R), and the second heating unit 22 of the temperature gradient forming unit 20 is disposed on a side relatively close to the top plate 14 in the first mounting unit 11 (a side relatively far from the bottom plate 15 and a side relatively far from the rotating shaft R). In addition, in the main body 10 of the thermal cycler 1 illustrated in FIGS. 1 and 2, the third heating unit 23 of the temperature gradient forming unit 20 is disposed on a side relatively far from the top plate 14 in the second mounting unit 12 (a side relatively close to the bottom plate 15 and aside relatively far from the rotating shaft R), and the fourth heating unit 24 of the temperature gradient forming unit 20 is disposed on a side relatively close to the top plate 14 in the second mounting unit 12 (a side relatively far from the bottom plate 15 and a side relatively close to the rotating shaft R).

The first heating unit 21 sets a first area 111 of the flow path 110 of the reaction container 100 to a first temperature, when the reaction container 100 is mounted on the first mounting unit 11. In the example illustrated in FIG. 2, the first heating unit 21 is disposed at a position to heat the first area 111 of the reaction container 100 in the main body 10.

The first heating unit 21 may include a mechanism that generates heat and a member that transmits the generated heat to the reaction container 100. In the example illustrated in FIG. 2, the first heating unit 21 is configured to include a first heater 21a as the mechanism that generates heat and the first heat block 21b as the member that transmits the generated heat to the reaction container 100.

In the thermal cycler 1, the first heater 21a is a cartridge heater and is connected to an external power supply (not illustrated). The first heater 21a is not limited thereto, and a carbon heater, a sheet heater, an IH heater (electromagnetic induction heater), a Peltier element, a heating liquid, a heating gas, and the like may be used. The first heater 21a is inserted into the first heat block 21b, and as the first heater 21a generates heat, the first heat block 21b is heated. The first heat block 21b is a member that transmits the heat generated by the first heater 21a to the reaction container 100. In the thermal cycler 1, the first heat block 21b is a block made of aluminum. Since the cartridge heater facilitates temperature control, the cartridge heater is used as the first heater 21a, thereby easily stabilizing the temperature of the first heating unit 21. Therefore, more accurate thermal cycling can be realized.

The material of the heat block may be appropriately selected considering the conditions such as thermal conductivity, heat insulation, and workability. For example, since aluminum has a high thermal conductivity, the first heat block 21b may be made of aluminum to efficiently heat the reaction container 100. In addition, uneven heating of the heat block is less likely to occur, and thus thermal cycling with high accuracy can be realized. In addition, since work is easy, the first heat block 21b may be molded with good accuracy, thereby increasing accuracy in heating. Therefore, more accurate thermal cycling can be realized. In addition, the material of the heat block may use, for example, a copper alloy or may be a combination of a plurality of materials.

It is preferable that, when the reaction container 100 is mounted on the first mounting unit 11, the first heating unit 21 come into contact with the reaction container 100. Accordingly, in a case where the reaction container 100 is heated by the first heating unit 21, heat from the first heating unit 21 may be more stably transmitted to the reaction container 100 than a configuration in which the first heating unit 21 does not come into contact with the reaction container 100, thereby stabilizing the temperature of the reaction container 100. As in this embodiment, in the case where the first mounting unit 11 is formed as a part of the first heating unit 21, it is preferable that the first mounting unit 11 come into contact with the reaction container 100. Accordingly, heat from the first heating unit 21 may be stably transmitted to the reaction container 100, thereby efficiently heating the reaction container 100.

When the reaction container 100 is mounted on the first mounting unit 11, the second heating unit 22 sets a second area 112 of the flow path 110 of the reaction container 100, which is closer to the top plate 14 than the first area 111, to a second temperature different from the first temperature. In the example illustrated in FIG. 2, the second heating unit 22 is disposed at a position to heat the second area 112 of the reaction container 100 in the main body 10. The second heating unit 22 includes a second heater 22a and the second heat block 22b. The configuration of the second heating unit 22 in this embodiment is the same as that of the first heating unit 21 except that the area of the reaction container 100 to be heated and the heating temperature are different from those of the first heating unit 21. Alternatively, the first and second heating units 21 and 22 may employ different heating mechanisms. In addition, the first heat block 21b and the second heat block 22b may be made of different materials.

When the reaction container 100 is mounted on the second mounting unit 12, the third heating unit 23 sets the first area 111 of the flow path 110 of the reaction container 100 to the first temperature. In the example illustrated in FIG. 2, the third heating unit 23 is disposed at the position to heat the first area 111 of the reaction container 100 in the main body 10. The third heating unit 23 includes a third heater 23a and the third heat block 23b. The configuration of the third heating unit 23 in this embodiment is the same as that of the first heating unit 21 except that the area of the reaction container 100 to be heated is different from that of the first heating unit 21. Alternatively, a different heating mechanism from the first heating unit 21 may be employed as the third heating unit 23. In addition, the first heat block 21b and the third heat block 23b may be made of different materials.

When the reaction container 100 is mounted on the second mounting unit 12, the fourth heating unit 24 sets the second area 112 of the flow path 110 of the reaction container 100, which is closer to the top plate 14 than the first area 111, to the second temperature different from the first temperature. In the example illustrated in FIG. 2, the fourth heating unit 24 is disposed at the position to heat the second area 112 of the reaction container 100 in the main body 10. The fourth heating unit 24 includes a fourth heater 24a and the fourth heat block 24b. The configuration of the fourth heating unit 24 in this embodiment is the same as that of the first heating unit 21 except that the area of the reaction container 100 to be heated and the heating temperature are different from those of the first heating unit 21. Alternatively, a different heating mechanism from the first heating unit 21 may be employed as the fourth heating unit 24. In addition, the first heat block 21b and the fourth heat block 24b may be made of different materials.

The first heating unit 21 and the second heating unit 22 are provided in the main body 10 to be separated from each other. In addition, the third heating unit 23 and the fourth heating unit 24 are provided in the main body 10 to be separated from each other. Accordingly, the first and second heating units 21 and 22, and the third and fourth heating units 23 and 24, which are controlled at different temperatures, are difficult to affect each other, and thus the temperatures of the first, second, third, and fourth heating units 21, 22, 23, and 24 are easily stabilized. A spacer may be provided between the first and second heating units 21 and 22 and between the third and fourth heating units 23 and 24. In the main body 10 of the thermal cycler 1, the first, second, third, and fourth heating units 21, 22, 23, and 24 are fixed to the frame 13, the top plate 14, the bottom plate 15, a side plate 16, and a side plate 17 in their peripheries. In addition, as long as a temperature gradient is formed to a degree at which desired reaction accuracy can be ensured, the number of heating units may be an arbitrary number.

In other words, the thermal cycler 1 according to this embodiment includes the first and second heating units 21 and 22 provided to be separated from each other in the mounting direction of the first mounting unit 11, and the third and fourth heating units 23 and 24 provided to be separated from each other in the mounting direction of the second mounting unit 12, sets the first and third heating units 21 and 23 to the first temperature, sets the second and fourth heating units 22 and 24 to the second temperature different from the first temperature, provides the first heating unit 21 on the side closer to the rotating shaft R than the second heating unit 22, and provides the fourth heating unit 24 on the side closer to the rotating shaft R than the third heating unit 23.

At least one of the first and second heating units 21 and 22 and at least one of the third and fourth heating units 23 and 24 may have a plurality of modes having different temperatures (operation modes). Accordingly, the thermal cycler 1 capable of realizing various thermal cycles such as a plurality of thermal cycles having different temperature conditions and a thermal cycle in which the temperature conditions are changed partway can be realized.

The temperatures of the first, second, third, and fourth heating units 21, 22, 23, and 24 are controlled by temperature sensors (not illustrated) and a control unit 40 described later. It is preferable that the temperatures of the first, second, third, and fourth heating units 21, 22, 23, and 24 be set to heat the reaction container 100 to the desired temperature. Details of control of the temperatures of the first, second, third, and fourth heating units 21, 22, 23, and 24 will be provided in detail in section "3. Example of Control of Thermal Cycler". In addition, the temperatures of the first, second, third, and fourth heating units 21, 22, 23, and 24 may be controlled to heat the first and second areas 111 and 112 of the reaction container 100 to the desired temperatures. For example, considering the material and size of the reaction container 100, the temperatures of the first and second areas 111 and 112 may be heated to the desired temperatures more accurately. In this embodiment, the temperatures of the first, second, third, and fourth heating units 21, 22, 23, and 24 are measured by the temperature sensors. The temperature sensor in this embodiment is a thermocouple. In addition, the temperature sensor is not limited thereto, and for example, a thermometric resistor or a thermistor may be used.

The driving mechanism 30 is a mechanism which rotates the first mounting unit 11, the second mounting unit 12, and the temperature gradient forming unit 20 (the first, second, third, and fourth heating units 21, 22, 23, and 24) around the rotating shaft R having a component perpendicular to the direction in which gravity is applied and a component intersecting the mounting directions of the first and second mounting units 11 and 12. That is, the driving mechanism 30 is a mechanism which rotates the first mounting unit 11, the second mounting unit 12, and the temperature gradient forming unit 20 (the first, second, third, and fourth heating units 21, 22, 23, and 24) around the rotating shaft R having a component perpendicular to the direction in which gravity is applied and a component perpendicular to the direction in which the reaction liquid 140 moves along the flow path 110 when the reaction containers 100 are mounted on the first and second mounting units 11 and 12.

The direction "having a component perpendicular to the direction in which gravity is applied" is a direction having a component perpendicular to the direction in which gravity is applied, from the vector sum of "a component parallel to the direction in which gravity is applied" and "a component perpendicular to the direction in which gravity is applied".

The direction "having a component intersecting the mounting direction of the first and second mounting units 11 and 12 is a direction having a component intersecting the mounting direction of the first and second mounting units 11 and 12 from the vector sum of "a component parallel to the mounting direction of the first and second mounting units 11 and 12" and "a component perpendicular to the mounting direction of the first and second mounting units 11 and 12".

The direction "having a component perpendicular to the direction in which the reaction liquid 140 moves along the flow path 110" is a direction having a component perpendicular to the direction in which the reaction liquid 140 moves along the flow path 110 from the vector sum of "a component parallel to the direction in which the reaction liquid 140 moves along the flow path 110" and "a component perpendicular to the direction in which the reaction liquid 140 moves along the flow path 110".

In the thermal cycler 1 according to this embodiment, the driving mechanism 30 rotates the first mounting unit 11, the second mounting unit 12, and the temperature gradient forming unit 20 (the first, second, third, and fourth heating units 21, 22, 23, and 24) around the same rotating shaft R. In the thermal cycler 1 according to this embodiment, the driving mechanism 30 rotates the arrangement of the first mounting unit 11, the second mounting unit 12, and the temperature gradient forming unit 20 (the first, second, third, and fourth heating units 21, 22, 23, and 24) between a first arrangement and a second arrangement in which the position of the lowermost point of the first and second mounting units 11 and 12 is different from that of the first arrangement.

In addition, in this embodiment, the driving mechanism 30 includes a motor and a driving shaft (not illustrated), and the driving shaft is configured to be connected to the side plate 17 of the main body 10. When the motor of the driving mechanism 30 is operated, the main body 10 is rotated around the driving shaft as the rotating shaft R. In this embodiment, the six first mounting units 11 and the six second mounting units 12 are provided along the direction of the rotating shaft R. In addition, the driving mechanism 30 is not limited to the motor, and may employ, for example, a handle or a spiral spring.

The thermal cycler 1 may not include the control unit 40. The control unit 40 controls the driving mechanism 30. In this embodiment, the control unit 40 controls the driving mechanism 30 to rotate the arrangement of the first mounting unit 11, the second mounting unit 12, and the temperature gradient forming unit 20 (the first, second, third, and fourth heating units 21, 22, 23, and 24) between the first arrangement and the second arrangement different from the first arrangement. That is, the control unit 40 controls the driving mechanism 30 to rotate the arrangement of the first mounting unit 11, the second mounting unit 12, and the temperature gradient forming unit 20 (the first, second, third, and fourth heating units 21, 22, 23, and 24) between the first arrangement and the second arrangement in which the position of the lowermost point in the flow path 110 in the direction in which gravity is applied is different from that of the first arrangement. In this embodiment, in a case of a rotation from the first arrangement to the second arrangement and in a case of a rotation from the second arrangement to the first arrangement, the control unit 40 controls the driving mechanism 30 to rotate the first mounting unit 11, the second mounting unit 12, and the temperature gradient forming unit 20 (the first, second, third, and fourth heating units 21, 22, 23, and 24) in the reverse directions.

The control unit 40 may further control the temperature gradient forming unit 20 (the first, second, third, and fourth heating units 21, 22, 23, and 24).

An example of control by the control unit 40 is described in detail in section "3. Example of Control of Thermal Cycler". The control unit 40 may be realized by a dedicated circuit and configured to perform control described later. In addition, for example, the control unit 40 may function as a computer in which a CPU (Central Processing Unit) executes control programs stored in a storage device such as a ROM (Read Only Memory) or a RAM (Random Access Memory) and may be configured to perform control described later. In this case, the storage device may have a work area that temporarily stores intermediate data during control, controls results, and the like. In addition, the control unit 40 may also have a timer for measuring time. The control unit 40 may control the first, second, third, and fourth heating units 21, 22, 23, and 24 to desired temperatures according to the outputs of the temperature sensors (not illustrated) described above.

It is preferable that the thermal cycler 1 include a structure in which the reaction containers 100 are held at predetermined positions with respect to the first, second, third, and fourth heating units 21, 22, 23, and 24. Accordingly, predetermined areas of the reaction container 100 can be heated by the first, second, third, and fourth heating units 21, 22, 23, and 24. In this embodiment, by appropriately setting the sizes of the through-holes (the diameters of the first and second mounting units 11 and 12) provided in the first, second, third, and fourth heat blocks 21b, 22b, 23b, and 24b, the reaction containers 100 are held at the predetermined positions with respect to the first, second, third, and fourth heating units 21, 22, 23, and 24.

Figure 3:
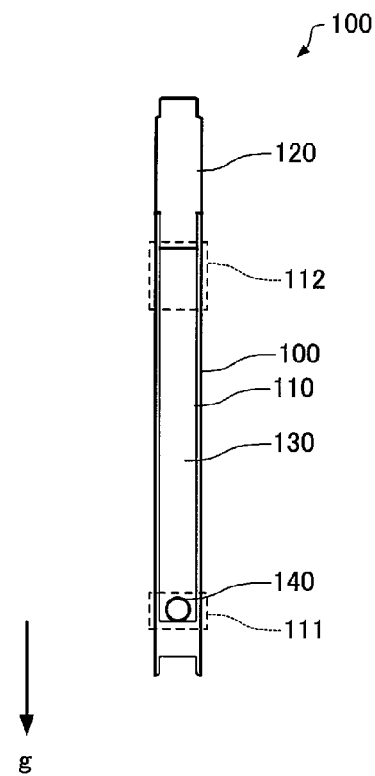
FIG. 3 is a cross-sectional view illustrating the configuration of a reaction container mounted on the thermal cycler according to the embodiment.

2. Configuration of Reaction Container Mounted on Thermal Cycler According to this Embodiment FIG. 3 is a cross-sectional view illustrating the configuration of the reaction container 100 mounted on the thermal cycler 1 according to this embodiment. In FIG. 3, the arrow g indicates a direction in which gravity is applied.

The reaction container 100 is filled with the reaction liquid 140 and a liquid 130 that has a different specific gravity from the reaction liquid 140 and is not blended with the reaction liquid 140 (hereinafter, referred to as a "liquid 130"), and includes the flow path 110 in which the reaction liquid 140 moves along opposing inner walls. In this embodiment, the liquid 130 is a liquid that has a smaller specific gravity than that of the reaction liquid 140 and is not blended with the reaction liquid 140. In addition, as the liquid 130, for example, a liquid that is not blended with the reaction liquid 140 and has a higher specific gravity than that of the reaction liquid 140 may also be employed. In the example illustrated in FIG. 3, the reaction container 100 includes the flow path 110 and a sealing unit 120. The flow path 110 is filled with the reaction liquid 140 and the liquid 130 and is sealed by the sealing unit 120.

The flow path 110 is formed so that the reaction liquid 140 moves along the opposing inner walls. Here, the "opposing inner walls" of the flow path 110 means two areas having a facing positional relationship in the wall surfaces of the flow path 110. In addition, "along" means a state where the distance between the reaction liquid 140 and the wall surfaces of the flow path 110 is small, and includes a state where the reaction liquid 140 comes into contact with the wall surfaces of the flow path 110. Therefore, "the reaction liquid 140 moves along the opposing inner walls" means "the reaction liquid 140 moves in a state of having small distances from both the two areas having a facing positional relationship in the wall surfaces of the flow path 110". In other words, the distances from the two opposing inner walls of the flow path 110 are distances to a degree at which the reaction liquid 140 moves along the inner walls.

The flow path 110 of the reaction container 100 having such a shape can restrict the direction in which the reaction liquid 140 moves in the flow path 110, and thus a path on which the reaction liquid 140 moves in the flow path 110 can be defined to a certain extent. Accordingly, a time taken for the reaction liquid 140 to move in the flow path 110 can be limited to a certain range. Therefore, it is preferable that the distance between the two opposing inner walls of the flow path 110 be set to a degree at which variations of thermal cycling conditions performed on the reaction liquid 140, which are caused by variations of the time for which the reaction liquid 140 moves in the flow path 110, that is, a degree at which the reaction results satisfy a desired accuracy. More specifically, it is preferable that the distance in the direction perpendicular to the direction in which the reaction liquid 140 in the two opposing inner walls of the flow path 110 moves be set to a degree at which two or more liquid droplets of the reaction liquid 140 are not able to be put therein.

In the example illustrated in FIG. 3, the external form of the reaction container 100 is a columnar shape, and the flow path 110 having a direction along the center axis (the vertical direction in FIG. 3) as the longitudinal direction is formed. The shape of the flow path 110 is a columnar shape in which the cross-section in a direction perpendicular to the longitudinal direction of the flow path 110, that is, the cross-section perpendicular to the direction in which the reaction liquid 140 moves in the area where the flow path 110 is present (this is the "cross-section" of the flow path 110) is circular. Therefore, the opposing inner walls of the flow path 110 in the reaction container 100 are areas including two points on the wall surface of the flow path 110, which oppose each other with the center of the cross-section of the flow path 110 interposed therebetween. In addition, "the direction in which the reaction liquid 140 moves" is the longitudinal direction of the flow path 110.

In addition, the shape of the flow path 110 is not limited to the columnar shape, and for example, may be a frustum shape. In addition, the cross-sectional shape of the flow path 110 is not limited to a circular shape, and is an arbitrary shape including polygons, ellipses, and the like as long as the reaction liquid 140 can move along the opposing inner walls. For example, in a case where the cross-section of the flow path 110 of the reaction container 100 is polygonal, "the opposing inner walls" are opposing inner walls of the flow path when a flow path in which the cross-section that is inscribed in the flow path 110 is circular is assumed. That is, the flow path 110 may be formed so that the reaction liquid 140 moves along the opposing inner walls of a virtual flow path in which the cross-section that is inscribed in the flow path 110 is circular. Accordingly, even in the case where the cross-section of the flow path 110 is polygonal, a path on which the reaction liquid 140 moves between the first and second areas 111 and 112 may be defined to a certain extent. Therefore, a time for the reaction liquid 140 to move between the first and second areas 111 and 112 can be limited to a certain range.

The first area 111 of the reaction container 100 is a partial area of the flow path 110 heated by the first heating unit 21 or the third heating unit 23. The second area 112 is a partial area of the flow path 110 different from the first area 111, which is heated by the second heating unit 22 or the fourth heating unit 24. In the example illustrated in FIG. 3, the first area 111 is an area including one end in the longitudinal direction of the flow path 110, and the second area 112 is an area including the other end in the longitudinal direction of the flow path 110. In the example illustrated in FIG. 3, an area surrounded by the dotted line including an end portion in the flow path 110 on a side relatively far from the sealing portion 120 is the first area 111, and an area surrounded by the dotted line including an end portion in the flow path 110 on a side relatively close to the sealing portion 120 is the second area 112. In the thermal cycler 1 according to this embodiment, the first or third heating unit 21 or 23 heats the first area 111 of the reaction container 100, and the second or fourth heating unit 22 or 24 heats the second area 112 of the reaction container 100, such that a temperature gradient is formed in the direction in which the reaction liquid 140 moves with respect to the flow path 110 of the reaction container 100.

The flow path 110 is filled with the liquid 130 and the reaction liquid 140. Since the liquid 130 has an unblendable property of not being blended with the reaction liquid 140, as illustrated in FIG. 3, the reaction liquid 140 is held in a state of liquid droplets in the liquid 130. Since the reaction liquid 140 has a greater specific gravity than the liquid 130, the reaction liquid 140 is positioned in the area of the lowermost portion of the flow path 110 in the direction in which gravity is applied. As the liquid 130, for example, dimethyl silicone oil or paraffin oil may be used. The reaction liquid 140 is a liquid containing components necessary for the reaction. For example, in a case where the reaction is PCR, the reaction liquid 140 contains DNA as an amplification object, DNA polymerase (PCR enzyme) needed to amplify the DNA, primers, a fluorescent probe in which the intensity of light having a predetermined wavelength (light emitted by the fluorescent probe) is changed by complementarily binding to a specific DNA sequence, and the like. Otherwise, for example, in a case where the reaction is RT-PCR, the reaction liquid 140 contains reverse transcriptase, RNA which is a template of reverse transcription, DNA polymerase (PCR enzyme) needed to amplify reverse transcribed cDNA, primers, a fluorescent probe in which the intensity of light having a predetermined wavelength is changed by complementarily binding to a specific DNA sequence, and the like. For example, in a case where PCR is performed using an oil as the liquid 130, it is preferable that the reaction liquid 140 be an aqueous solution containing the above-described components.

3. Example of Control of Thermal Cycler

Figure 4:
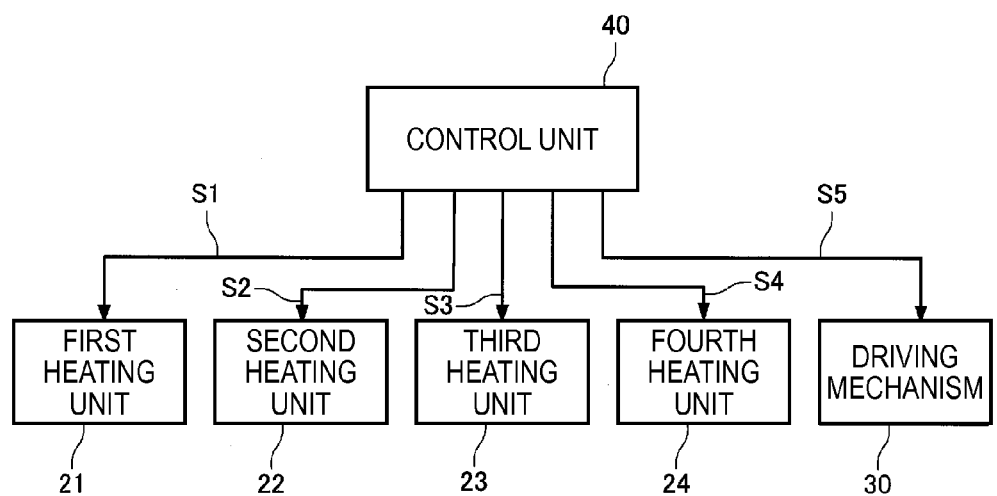
FIG. 4 is a function block diagram of the thermal cycler according to the embodiment.

FIG. 4 is a function block diagram of the thermal cycler 1 according to this embodiment. The control unit 40 outputs a control signal S1 to the first heating unit 21 to control the temperature of the first heating unit 21. The control unit 40 outputs a control signal S2 to the second heating unit 22 to control the temperature of the second heating unit 22. The control unit 40 outputs a control signal S3 to the third heating unit 23 to control the temperature of the third heating unit 23. The control unit 40 outputs a control signal S4 to the fourth heating unit 24 to control the temperature of the fourth heating unit 24. The control unit 40 outputs a control signal S5 to the driving mechanism 30 to control the driving mechanism 30.

Next, an example of control of the thermal cycler 1 according to this embodiment will be described. Hereinafter, control to rotate the arrangement of the first mounting unit 11, the second mounting unit 12, and the temperature gradient forming unit 20 (the first, second, third, and fourth heating units 21, 22, 23, and 24) between the first arrangement in which the position of the lowermost point of the flow path 110 in the direction in which gravity is applied is in the first area 111 when the reaction containers 100 are mounted on the first and second mounting units 11 and 12, and the second arrangement in which the position of the lowermost point of the flow path 110 in the direction in which gravity is applied is in the second area 112 is exemplified.

Figure 5A:
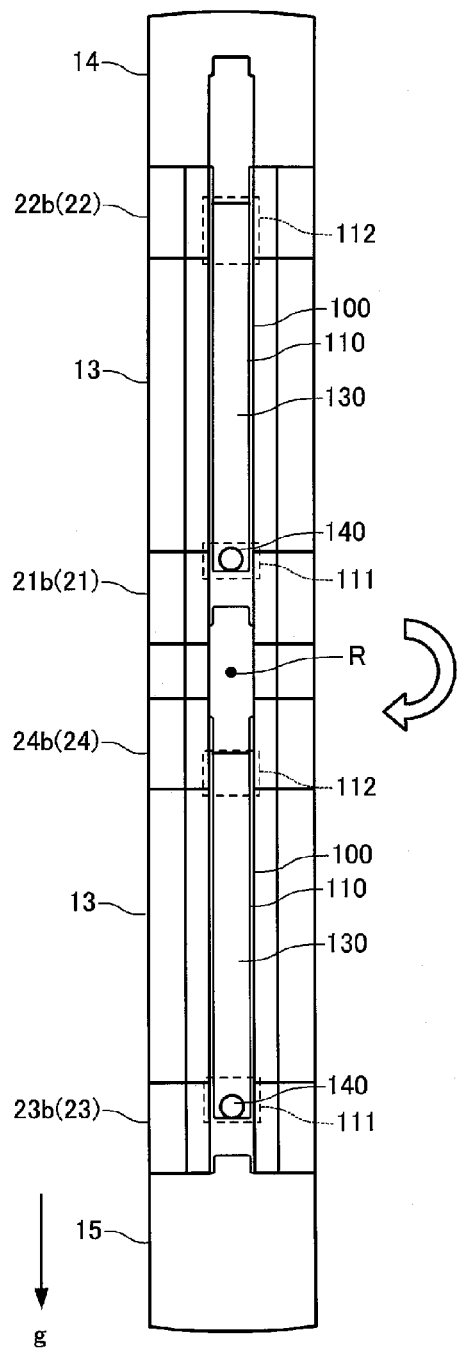
FIG. 5A is a cross-sectional view schematically illustrating the cross-section in a surface perpendicular to a rotating shaft R taken along the line A-A of FIG. 1A in a first arrangement.
Figure 5B:
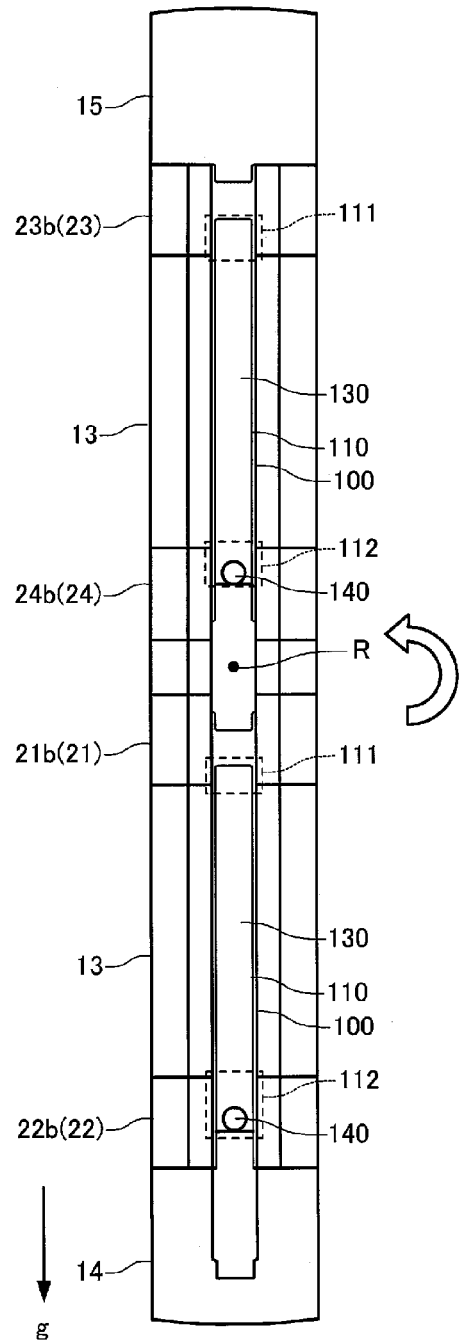
FIG. 5B is a cross-sectional view schematically illustrating the cross-section in a surface perpendicular to the rotating shaft taken along the line A-A of FIG. 1A in a second arrangement.

FIG. 5A is a cross-sectional view schematically illustrating the cross-section in a surface perpendicular to the rotating shaft R taken along the line A-A of FIG. 1A in the first arrangement, and FIG. 5B is a cross-sectional view schematically illustrating the cross-section in a surface perpendicular to the rotating shaft R taken along the line A-A of FIG. 1A in the second arrangement. In FIGS. 5A and 5B, the outlined arrow indicates the rotational direction of the main body 10, and the arrow g indicates the direction in which gravity is applied.

As illustrated in FIG. 5A, the first arrangement is an arrangement in which the first area 111 is positioned at the lowermost portion of the flow path 110 in the direction in which gravity is applied, in the case where the reaction containers 100 are mounted on the first and second mounting units 11 and 12. In the example illustrated in FIG. 5A, in the first arrangement, the reaction liquid 140 having a greater specific gravity than the liquid 130 is present in the first area 111. In addition, as illustrated in FIG. 5B, the second arrangement is an arrangement in which the second area 112 is positioned at the lowermost portion of the flow path 110 in the direction in which gravity is applied, in the case where the reaction containers 100 are mounted on the first and second mounting units 11 and 12. In the example illustrated in FIG. 5B, in the second arrangement, the reaction liquid 140 having a greater specific gravity than the liquid 130 is present in the second area 112.

In this manner, the driving mechanism 30 rotates the first mounting unit 11, the second mounting unit 12, and the temperature gradient forming unit 20 between the first arrangement and the second arrangement different from the first arrangement, so that thermal cycling can be performed on the reaction liquid 140.

According to this embodiment, since the rotating shaft R has the component perpendicular to the direction in which gravity is applied and the component orthogonal to the mounting directions of the first and second mounting units 11 and 12, when the driving mechanism 30 rotates the first and second mounting units 11 and 12, the position of the lowermost point or the uppermost point in the flow path 110 of the reaction container 100 in the direction in which gravity is applied is changed, in the case where the reaction containers 100 are mounted on the first and second mounting units 11 and 12. Accordingly, the reaction liquid 140 moves in the flow path 110 of the reaction container 100 having a temperature gradient formed by the temperature gradient forming unit 20 (the first, second, third, and fourth heating units 21, 22, 23, and 24). Therefore, thermal cycling can be performed on the reaction liquid 140 that fills the reaction container 100.

In addition, while the driving mechanism 30 holds the first mounting unit 11, the second mounting unit 12, and the temperature gradient forming unit 20 (the first, second, third, and fourth heating units 21, 22, 23, and 24) in a predetermined arrangement, the reaction liquid 140 can be held at a predetermined temperature. For example, by switching the arrangements of the first mounting unit 11, the second mounting unit 12, and the temperature gradient forming unit 20 (the first, second, third, and fourth heating units 21, 22, 23, and 24), a state where the reaction container 100 is held in the first arrangement and a state where the reaction container 100 is held in the second arrangement can be switched. The first arrangement is an arrangement in which the first area 111 of the flow path 110 included in the reaction container 100 is positioned at the lowermost portion of the flow path 110 in the direction in which gravity is applied. The second arrangement is an arrangement in which the second area 112 of the flow path 110 included in the reaction container 100 is positioned at the lowermost portion of the flow path 110 in the direction in which gravity is applied. That is, in the case where the specific gravity of the reaction liquid 140 is greater than the liquid 130, the reaction liquid 140 in the first arrangement can be held in the first area 111 and the reaction liquid 140 in the second arrangement can be held in the second area 112 by the action of gravity. Since the first area 111 is heated by the first heating unit 21, and the second area 112 is heated by the second heating unit 22, the first area 111 and the second area 112 can be set to different temperatures. Therefore, while the reaction container 100 is held in the first or second arrangement, the reaction liquid 140 can be held at a predetermined temperature, so that the thermal cycler 1 capable of easily controlling a heating time can be provided.

In addition, the first and second mounting units 11 and 12 are disposed on the opposite sides with the rotating shaft R interposed therebetween, the mounting direction of the first mounting unit 11 and the mounting direction of the second mounting unit 12 are in the same direction, and the temperature gradient forming unit 20 (the first, second, third, and fourth heating units 21, 22, 23, and 24) forms a temperature gradient in the same direction with respect to the reaction container 100 mounted on the first mounting unit 11 and the reaction container 100 mounted on the second mounting unit 12. Therefore, reactions having the same time conditions can be performed at the same timing using the reaction container 100 mounted on the first mounting unit 11 and the reaction container 100 mounted on the second mounting unit 12. The first and second mounting units 11 and 12 do not need to be provided separately in the direction along the rotating shaft R. Therefore, the thermal cycler 1 that is appropriate for a size reduction can be realized.

In the case of a rotation from the first arrangement to the second arrangement and in the case of a rotation from the second arrangement to the first arrangement, the control unit 40 may control the driving mechanism 30 to rotate the first mounting unit 11, the second mounting unit 12, and the temperature gradient forming unit 20 (the first, second, third, and fourth heating units 21, 22, 23, and 24) in the opposite direction. Accordingly, a mechanism for reducing twisting of wiring caused by the rotations is unnecessary. Therefore, the thermal cycler 1 that is appropriate for a size reduction can be realized. In addition, it is preferable that the number of revolutions in the case of the rotation from the first arrangement to the second arrangement and the number of revolutions in the case of the rotation from the second arrangement to the first arrangement be less than one revolution (a rotational angle is less than 360°). Accordingly, the degree of wire being twisted can be reduced.

The control unit 40 may control the first and third heating units 21 and 23 to the first temperature and the second temperature different from the first temperature, and may control the second and fourth heating units 22 and 24 to a third temperature different from the first and second temperatures.

That is, the control unit 40 has a mode of controlling the first and third heating units 21 and 23 to the first temperature and a mode of controlling the first and third heating units 21 and 23 to the second temperature, and controls the second and fourth heating units 22 and 24 to the third temperature. Since the first, second, and third temperatures are different from each other, thermal cycling having a combination of at least three types of temperatures can be realized by the first and second heating units 21 and 22.

Figure 6:
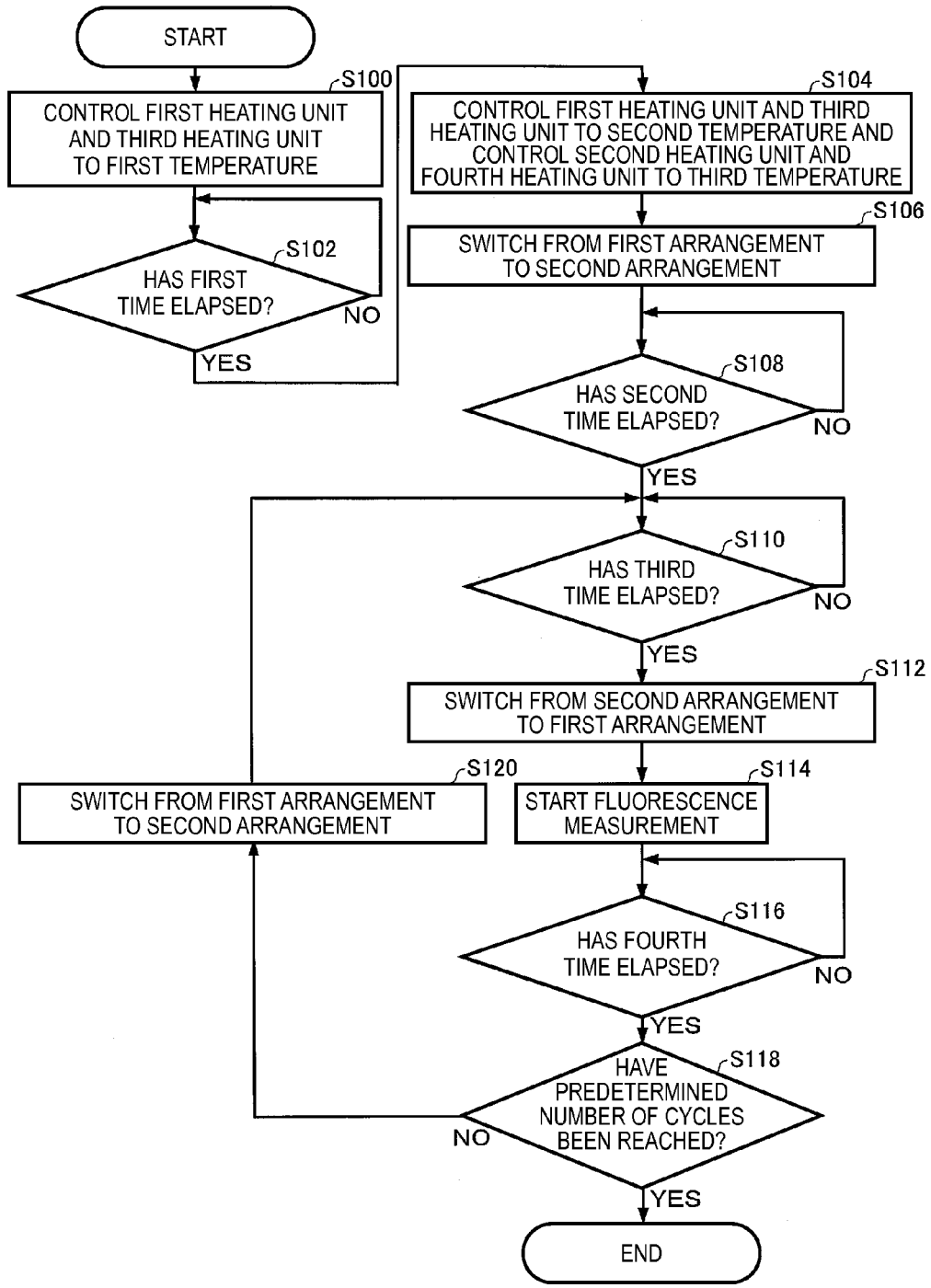
FIG. 6 is a flowchart illustrating a specific example of a control method of the thermal cycler according to the embodiment.

Next, a specific example of a control method of the thermal cycler 1 will be described by exemplifying a case where real-time measurement is performed using RT-PCR including a hot-start process (a process of activating a hot-start enzyme by heat in PCR using a hot-start PCR enzyme). In addition, a fluorescent probe in which the intensity of light having a predetermined wavelength is changed by complementarily binding to a specific DNA sequence is contained in the reaction liquid 140. FIG. 6 is a flowchart illustrating the specific example of the control method of the thermal cycler 1 according to this embodiment. Hereinafter, an example in which Step S100 is performed after mounting the reaction containers 100 to the first and second mounting units 11 and 12 is described, but the reaction containers 100 may also be mounted on the first and second mounting units 11 and 12 after Step S100.

In this specific example, first, the control unit 40 performs a first treatment in which, in a case where the first and third heating units 21 and 23 are controlled to the first temperature and a first time has elapsed while the arrangement of the first mounting unit 11, the second mounting unit 12, and the temperature gradient forming unit 20 is the first arrangement, the first and third heating units 21 and 23 are controlled to the second temperature higher than the first temperature, the second and fourth heating units 22 and 24 are controlled to the third temperature higher than the second temperature, and the driving mechanism 30 is controlled to switch the arrangement of the first mounting unit 11, the second mounting unit 12, and the temperature gradient forming unit 20 from the first arrangement to the second arrangement.

More specifically, first, the control unit 40 outputs the control signal S1 to the first heating unit 21 to control the temperature of the first heating unit 21 to the first temperature, and outputs the control signal S3 to the third heating unit 23 to control the temperature of the third heating unit 23 to the first temperature (Step S100). In the specific example, the first temperature is a temperature at which a reverse transcription reaction proceeds by reverse transcriptase. The "temperature at which a reverse transcription reaction proceeds by reverse transcriptase" is a temperature that is dependent on the type of reverse transcriptase, and is generally in a range of about 20° C. or higher and 70° C. or less. In general, reaction easily proceeds in a temperature range of particularly about 40° C. or higher and 50° C. or less. In addition, in the specific example, the arrangement of the first mounting unit 11, the second mounting unit 12, and the temperature gradient forming unit 20 in an initial operation is the first arrangement. Therefore, the reaction liquid 140 is held in the first area 111. That is, the reaction liquid 140 is held at the first temperature.

In addition, in Step S100, the control unit 40 may output the control signal S2 to the second heating unit 22 and output the control signal S4 to the fourth heating unit 24 to control the temperatures of the second and fourth heating units 22 and 24 to a temperature at which reverse transcriptase is not deactivated. The "temperature at which reverse transcriptase is not deactivated" is a temperature that is dependent on the type of reverse transcriptase, and is generally in a range of about 20° C. or higher and 70° C. or less. In general, at a temperature higher than 70° C., reverse transcriptase is deactivated or easily deteriorated. By controlling the temperatures of the second and fourth heating units 22 and 24 to the temperature at which reverse transcriptase is not deactivated, the reaction liquid 140 is less likely to be exposed to the temperature at which reverse transcriptase is not deactivated, when the reaction containers 100 are mounted on the first and second mounting units 11 and 12.

After Step S100, the control unit 40 determines whether or not the first time has elapsed after Step S100 is ended (after the first and third heating units 21 and 23 reach the first temperature) (Step S102). In the specific example, the first time is a time needed for the reverse transcription reaction. In a case where the control unit 40 determines that the first time has not elapsed (in a case of NO in Step S102), the control unit 40 repeats Step S102.

In a case where the control unit 40 determines that the first time has elapsed (in a case of YES in Step S102), the control unit 40 outputs the control signal S1 to the first heating unit 21 to control the temperature of the first heating unit 21 to the second temperature, outputs the control signal S3 to the third heating unit 23 to control the temperature of the third heating unit 23 to the second temperature, outputs the control signal S2 to the second heating unit 22 to control the temperature of the second heating unit 22 to the third temperature, and outputs the control signal S4 to the fourth heating unit 24 to control the temperature of the fourth heating unit 24 to the third temperature (Step S104). In the specific example, the second temperature is an annealing and elongation temperature in PCR. The "annealing and elongation temperature in PCR" is a temperature that is dependent on the type of enzyme used to amplify nucleic acid (in the specific example, DNA polymerase), and is generally in a range of about 50° C. or higher and 70° C. or less. In the specific example, the third temperature is a thermal denaturation temperature in PCR. The "thermal denaturation temperature in PCR" is a temperature that is dependent on the type of enzyme used to amplify nucleic acid, and is generally in a range of about 90° C. or higher and 100° C. or less.

After Step S104, the control unit 40 outputs the control signal S5 to the driving mechanism 30 to control the driving mechanism 30 to switch the arrangement of the first mounting unit 11, the second mounting unit 12, and the temperature gradient forming unit 20 from the first arrangement to the second arrangement (Step S106). As described above, the arrangement of the first mounting unit 11, the second mounting unit 12, and the temperature gradient forming unit 20 is the first arrangement until Step S104. Therefore, by performing Step S102, the arrangement of the first mounting unit 11, the second mounting unit 12, and the temperature gradient forming unit 20 is switched to the second arrangement. In the case where the arrangement of the first mounting unit 11, the second mounting unit 12, and the temperature gradient forming unit 20 is the second arrangement, the reaction liquid 140 is held in the second area 112. That is, the reaction liquid 140 is held at the third temperature.

After Step S106, the control unit 40 performs a second treatment in which a second time has elapsed while the arrangement of the first mounting unit 11, the second mounting unit 12, and the temperature gradient forming unit 20 is the second arrangement.

More specifically, after Step S106, the control unit 40 determines whether or not the second time has elapsed after Step S106 is ended (Step S108). In the specific example, the second time is a time needed for activation (hot-start) of PCR enzyme. In a case where the control unit 40 determines that the second time has not elapsed (in a case of NO in Step S108), the control unit 40 repeats Step S108.

In a case where the control unit 40 determines that the second time has elapsed (in a case of YES in Step S108), the control unit 40 performs a third treatment in which, in a case where a third time has elapsed while the arrangement of the first mounting unit 11, the second mounting unit 12, and the temperature gradient forming unit 20 is the second arrangement, the control unit 40 outputs the control signal S5 to the driving mechanism 30 to control the driving mechanism 30 to switch the arrangement of the first mounting unit 11, the second mounting unit 12, and the temperature gradient forming unit 20 from the second arrangement to the first arrangement.

More specifically, first, the control unit 40 determines whether or not the third time has elapsed after Step S108 is ended (Step S110). In the specific example, the third time is a time needed for thermal denaturation of DNA in PCR. In a case where the control unit 40 determines that the third time has not elapsed (in a case of NO in Step S110), the control unit 40 repeats Step S110. In a case where the control unit 40 determines that the third time has elapsed (in a case of YES in Step S110), the control unit 40 outputs the control signal S5 to the driving mechanism 30 to control the driving mechanism 30 to switch the arrangement of the first mounting unit 11, the second mounting unit 12, and the temperature gradient forming unit 20 from the second arrangement to the first arrangement (Step S112). In the case where the arrangement of the first mounting unit 11, the second mounting unit 12, and the temperature gradient forming unit 20 is the first arrangement, the reaction liquid 140 is held in the first area 111. That is, as a result of Step S112, the reaction liquid 140 is held at the second temperature.

According to the specific example, in the first, second, and third treatments, the temperature of the first heating unit 21 varies. As such, by performing the first, second, and third treatments having different temperature conditions, the reverse transcription reaction can be performed before PCR, so that the thermal cycler 1 that is appropriate for RT-PCR can be realized.

In addition, in the case where PCR including the hot-start process is performed, the temperature at which an PCR enzyme is activated is at the same degree as the thermal denaturation temperature. Therefore, by performing the second treatment, thermal cycling including hot-start PCR which is a process of activating the PCR enzyme can be realized.

In the specific example, after the third treatment, the intensity (luminance in the specific example) of light having a predetermined wavelength is measured by a measuring unit (not illustrated) (for example, a fluorescence detector). More specifically, after Step S112, the measuring unit starts fluorescence measurement (Step S114). The measuring unit performs fluorescence measurement on a plurality of reaction containers 100 while moving on, for example, a slide. In addition, the PCR results may be checked by another method such as electrophoresis without performing fluorescence measurement.

By measuring the intensity of light having the predetermined wavelength after the third treatment using the measuring unit, the intensity of light having the predetermined wavelength, which correlates with the amount of specific DNA, in a time period in which the reaction liquid 140 is held at the annealing and elongation temperature can be measured. Therefore, the thermal cycler 1 appropriate for real-time PCR can be realized.

In a case where a fourth time has elapsed while the arrangement of the first mounting unit 11, the second mounting unit 12, and the temperature gradient forming unit 20 is the first arrangement after the third treatment, the control unit 40 may repeat a fourth treatment in which the control signal S5 is output to the driving mechanism 30 to control the driving mechanism 30 to switch the arrangement of the first mounting unit 11, the second mounting unit 12, and the temperature gradient forming unit 20 from the first arrangement to the second arrangement, and the third treatment a predetermined times.

More specifically, first, after Step S114, the control unit 40 determines whether or not the fourth time has elapsed after Step S112 is ended (Step S116). In the specific example, the fourth time is a time needed for annealing and elongation in PCR. In a case where the control unit 40 determines that the fourth time has not elapsed (in a case of NO in Step S116), the control unit 40 repeats Step S116. In a case where the control unit 40 determines that the fourth time has elapsed (in a case of YES in Step S116), the control unit 40 determines whether or not a predetermined number of cycles have been reached (Step S118).

In a case where the control unit 40 determines that the predetermined number of cycles have not been reached (in a case of NO in Step S118), the control unit 40 outputs the control signal S5 to the driving mechanism 30 to control the driving mechanism 30 to switch the arrangement of the first mounting unit 11, the second mounting unit 12, and the temperature gradient forming unit 20 from the first arrangement to the second arrangement (Step S120). After Step S120, from Step S110 to Step S118 are repeated. Ina case where the control unit 40 determines that the predetermined number of cycles have been reached (in a case of YES in Step S118), the treatment is ended. In the specific example, ending of the treatment is determined based on the number of cycles. However, a process of determining whether or not the intensity of light having the predetermined wavelength, which is measured in Step S114 has reached a predetermined value may be added before Step S118 to end the treatment without performing Step S118 in a case where the intensity of light has reached the predetermined value.

In the third treatment, the reaction liquid 140 is held at the third temperature in the second arrangement until the third time has elapsed, and in the fourth treatment, the reaction liquid 140 is held at the second temperature in the first arrangement until the fourth time has elapsed. In this manner, by repeating the fourth treatment and the third treatment (more specifically, Step S120 and from Step S110 to Step S118), thermal cycling appropriate for PCR may be repeated a predetermined number of times.

4. Example

Hereinafter, the invention will be described in more detail using Example, but the invention is not limited to the Example.

In the Example, an example in which real-time measurement is performed by the thermal cycler 1 using RT-PCR including a hot-start process is described.

FIG. 7 is a table showing the composition of the reaction liquid 140 in the Example. In FIG. 7, "SuperScript III Platinum" was "SuperScript III Platinum One-Step Quantitative RT-PCR System with ROX ("Platinum" is a registered trademark, manufactured by Life Technologies Corporation.)", and contained a PCR enzyme and reverse transcriptase. As RNA, RNA extracted from a liquid of a human nasal cavity swab (human sample) was used. In addition, as a result of performing immunochromatography on the human sample using a commercially available kit ("ESPLINE Influenza A&B-N (ESPLINE is a registered trademark)", made by FUJIREBIO Inc.), influenza type A was positive. In addition, "type A positive" in immunochromatography does not specifically determine the following influenza type A (InfA).

FIG. 8 is a table showing the base sequences of forward primers (F primer), reverse primers (R primer), and probes (Probe) corresponding to influenza type A (InfA), swine influenza type A (SW InfA), swine influenza type H1 (SW H1), and ribonuclease P (RNase P). All of them are the same as the base sequences described in "CDC protocol of realtime RTPCR for swine influenza A (H1N1)" (World Health Organization, the first revised edition on Apr. 30, 2009). The measured fluorescent luminances of all the four types of probes (Probe) shown in FIG. 8 increase with amplification of nucleic acid.

The experiment order was as in the flowchart shown in FIG. 6, the first temperature was set to 45° C., the second temperature was set to 58° C., the third temperature was set to 98° C., the first time was set to 60 seconds, the second time was set to 10 seconds, the third time was set to 5 seconds, the fourth time was set to 30 seconds, and the number of cycles of the thermal cycling treatment was set to 50. In addition, the number of reaction containers 100 mounted on the first or second mounting unit 11 or 12 was 4 (Sample A to Sample D).

Sample A contains the forward primer, the reverse primer, and the fluorescent probe corresponding to the influenza type A (InfA). Sample B contains the forward primer, the reverse primer, and the fluorescent probe corresponding to the swine influenza type A (SW InfA). Sample C contains the forward primer, the reverse primer, and the fluorescent probe corresponding to the swine influenza type H1 (SW H1). Sample D contains the forward primer, the reverse primer, and the fluorescent probe corresponding to the ribonuclease P (RNase P).

FIG. 9 is a graph showing the relationship between the number of cycles of the thermal cycling treatment and the measured luminance in the Example. The horizontal axis of FIG. 9 represents the number of cycles of the thermal cycling treatment, and the vertical axis represents a relative value of the luminance.

As shown in FIG. 9, it can be seen that in all the Samples A to D, luminance rapidly increases from the vicinity where the number of cycles of the thermal cycling treatment is about 20 to 30. Accordingly, it can be seen that cDNA reverse transcribed from RNA as a template is amplified. The Sample D was subjected to an experiment of endogenous control, and since the luminance of the Sample D was increased, it could be confirmed that DNA (cDNA) derived from the human sample was amplified. Moreover, cDNA was amplified in the Samples A to D, it was seen that all RNAs of the influenza type A, the swine influenza type A, and the swine influenza type H1 were included in the human sample. This result matches the result of the immunochromatography. Therefore, it was confirmed that real-time measurement could be performed by the thermal cycler 1 according to this embodiment using RT-PCR including a hot-start process.

In addition, the embodiments and modification examples described above are examples, and the invention is not limited thereto. For example, an appropriate combination of the embodiments and the modification examples can be made.

The invention is not limited to the above-described embodiments and the example, and various modifications can further be made. For example, the invention includes substantially the same configuration (for example, configurations having the same functions, methods, and results, or configurations having the same purposes and effects) as the configurations described in the embodiments. In addition, the invention includes configurations in which parts that are not essential to the configurations described in the embodiments are substituted. In addition, the invention includes configurations that exhibit the same actions and effects as those of the configurations described in the embodiments and configurations that achieve the same objects. In addition, the invention includes configurations in which well-known techniques are added to the configurations described in the embodiments.

The entire disclosure of Japanese Patent Application No. 2012-129336, filed on Jun. 6, 2012 is expressly incorporated by reference herein.

What is claimed is:

1. A thermal cycler comprising:

a first mounting unit and a second mounting unit;

a temperature gradient forming unit which forms a temperature gradient along mounting directions of the first mounting unit and the second mounting unit;

a shaft having a rotational axis that is perpendicular to a direction in which gravity is applied and a mounting component intersecting the mounting directions of the first mounting unit and the second mounting unit; and a driving mechanism which rotates the shaft about the rotational axis such that the first mounting unit, the second mounting unit, and the temperature gradient forming unit rotate around the shaft about the rotational axis, wherein the first mounting unit and the second mounting unit are disposed on opposite sides to each other with the shaft interposed therebetween, the first mounting unit and the second mounting unit are each configured to receive a plurality of parallel reaction containers, and the mounting direction of the first mounting unit and the mounting direction of the second mounting unit are in the same direction and on the same straight line.

2. The thermal cycler according to claim 1, wherein the temperature gradient forming unit includes:

a first temperature setting unit and a second temperature setting unit located on the first mounting unit; and a third temperature setting unit and a fourth temperature setting unit located on the second mounting unit, wherein the first temperature setting unit is located closer to the shaft than the second temperature setting unit, and the fourth temperature setting unit is located closer to the rotating shaft than the third temperature setting unit, wherein the first temperature setting unit and the third temperature setting unit are set to a first temperature.

3. The thermal cycler according to claim 1, wherein the shaft inverts the first mounting unit, the second mounting unit, and the temperature gradient forming unit between a first arrangement and a second arrangement in which the position of lowermost points of the first and second mounting units in the second arrangement are different from that of the first arrangement.

4. The thermal cycler according to claim 1, further comprising:

a control unit which controls the driving mechanism, wherein the control unit rotates the first mounting unit, the second mounting unit, and the temperature gradient forming unit between a first arrangement and a second arrangement different from the first arrangement, and a first rotation direction in which the first mounting unit, the second mounting unit, and the temperature gradient forming unit are rotated from the first arrangement to the second arrangement is different from a second rotation direction in which the first mounting unit, the second mounting unit, and the temperature gradient forming unit are rotated from the second arrangement to the first arrangement.

5. The thermal cycler according to claim 4, wherein the position of lowermost points of the first and second mounting units in the second arrangement are different from that of the first arrangement.

6. The thermal cycler according to claim 4, wherein the first rotation direction is a reverse direction of the second rotation direction.

7. The thermal cycler according to claim 1, wherein the first mounting unit overlaps the second mounting unit in the direction in which gravity is applied when the arrangement is the first arrangement or the second arrangement.

8. The thermal cycler according to claim 1, wherein the shaft inverts the first mounting unit, the second mounting unit, the first heating unit, the second heating unit, the third heating unit, and the fourth heating unit between a first arrangement and a second arrangement in which the position of lowermost points of the first and second mounting units in the second arrangement are different from that of the first arrangement.

9. The thermal cycler according to claim 8, further comprising:

a control unit which controls the driving mechanism, wherein the control unit rotates the first mounting unit, the second mounting unit, the first heating unit, the second heating unit, the third heating unit, and the fourth heating unit between a first arrangement and a second arrangement different from the first arrangement, and a first rotation direction in which the first mounting unit, the second mounting unit, the first heating unit, the second heating unit, the third heating unit, and the fourth heating unit are rotated from the first arrangement to the second arrangement is different from a second rotation direction in which the first mounting unit, the second mounting unit, the first heating unit, the second heating unit, the third heating unit, and the fourth heating unit are rotated from the second arrangement to the first arrangement.

10. The thermal cycler according to claim 9, wherein the position of lowermost points of the first and second mounting units in the second arrangement are different from that of the first arrangement.

11. The thermal cycler according to claim 9, wherein the first direction is a reverse direction of the second direction.

12. A thermal cycler comprising:

a first mounting unit and a second mounting unit;

a first heating unit and a second heating unit provided to be separated from each other in a mounting direction of the first mounting unit;

a third heating unit and a fourth heating unit provided to be separated from each other in a mounting direction of the second mounting unit;

a shaft having a rotational axis that is perpendicular to a direction in which gravity is applied and a mounting component intersecting the mounting directions of the first mounting unit and the second mounting unit; and a driving mechanism which rotates the shaft about the rotational axis such that the first mounting unit, the second mounting unit, the first heating unit, the second heating unit, the third heating unit, and the fourth heating unit rotate around the shaft about the rotational axis, wherein the first mounting unit and the second mounting unit are disposed on opposite sides to each other with the shaft interposed therebetween, the first mounting unit and the second mounting unit are each configured to receive a plurality of parallel reaction containers, the mounting direction of the first mounting unit and the mounting direction of the second mounting unit are in the same direction and on the same straight line, the first heating unit and the third heating unit are set to a first temperature, the second heating unit and the fourth heating unit are set to a second temperature different from the first temperature, the first heating unit is provided on a side closer to the shaft than the second heating unit, and the fourth heating unit is provided on a side closer to the shaft than the third heating unit.

13. The thermal cycler according to claim 12, wherein the first mounting unit overlaps the second mounting unit in the direction in which gravity is applied when the arrangement is the first arrangement or the second arrangement.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: InfA Forward primer

<400> SEQUENCE: 1
gatcratcct gtcacctctg ac                                              22

<210> SEQ ID NO 2
<211> LENGTH: 24
<212> TYPE: DNA
<213> ORGANISM: Artificial Sequence
<220> FEATURE:
<223> OTHER INFORMATION: InfA Reverse primer

<400> SEQUENCE: 2
agggcattyt ggacaaakcg tcta                                            24

<210> SEQ ID NO 3
<211> LENGTH: 24
<212> TYPE: DNA
<213> ORGANISM: Artificial Sequence
<220> FEATURE:
<223> OTHER INFORMATION: InfA Fluorescent probe

<400> SEQUENCE: 3
tgcagtcctc gctcactggg cacg                                            24

<210> SEQ ID NO 4
<211> LENGTH: 23
<212> TYPE: DNA
<213> ORGANISM: Artificial Sequence
<220> FEATURE:
<223> OTHER INFORMATION: SW InfA Forward primer

<400> SEQUENCE: 4
gcacggtcag cacttatyct rag                                             23

<210> SEQ ID NO 5
<211> LENGTH: 23
<212> TYPE: DNA
<213> ORGANISM: Artificial Sequence
<220> FEATURE:
<223> OTHER INFORMATION: SW InfA Reverse primer

<400> SEQUENCE: 5
gtgrgctggg ttttcatttg gtc                                             23

<210> SEQ ID NO 6
<211> LENGTH: 29
<212> TYPE: DNA
<213> ORGANISM: Artificial Sequence
<220> FEATURE:
<223> OTHER INFORMATION: SW InfA Fluorescent Probe

<400> SEQUENCE: 6
cyactgcaag cccatacaca caagcagca                                       29

<210> SEQ ID NO 7
<211> LENGTH: 23
<212> TYPE: DNA
<213> ORGANISM: Artificial Sequence

```
<220> FEATURE:
<223> OTHER INFORMATION: SW H1 Foward primer

<400> SEQUENCE: 7
gtgctataaa caccagccty cca                                              23

<210> SEQ ID NO 8
<211> LENGTH: 24
<212> TYPE: DNA
<213> ORGANISM: Artificial Sequence
<220> FEATURE:
<223> OTHER INFORMATION: SW H1 Reverse primer

<400> SEQUENCE: 8
cgggatattc cttaatcctg trgc                                             24

<210> SEQ ID NO 9
<211> LENGTH: 30
<212> TYPE: DNA
<213> ORGANISM: Artificial Sequence
<220> FEATURE:
<223> OTHER INFORMATION: SW H1 Fluorescent Probe

<400> SEQUENCE: 9
cagaatatac atccrgtcac aattggaraa                                       30

<210> SEQ ID NO 10
<211> LENGTH: 19
<212> TYPE: DNA
<213> ORGANISM: Artificial Sequence
<220> FEATURE:
<223> OTHER INFORMATION: RNaseP Foward primer

<400> SEQUENCE: 10
agatttggac ctgcgagcg                                                   19

<210> SEQ ID NO 11
<211> LENGTH: 20
<212> TYPE: DNA
<213> ORGANISM: Artificial Sequence
<220> FEATURE:
<223> OTHER INFORMATION: RNaseP Reverse primer

<400> SEQUENCE: 11
gagcggctgt ctccacaagt                                                  20

<210> SEQ ID NO 12
<211> LENGTH: 23
<212> TYPE: DNA
<213> ORGANISM: Artificial Sequence
<220> FEATURE:
<223> OTHER INFORMATION: RNaseP Fluorescent Probe

<400> SEQUENCE: 12
ttctgacctg aaggctctgc gcg                                              23
```